United States Patent [19]

Krabetz et al.

[11] Patent Number: 4,620,035

[45] Date of Patent: Oct. 28, 1986

[54] PRODUCTION OF ACRYLIC ACID BY OXIDATION OF ACROLEIN

[75] Inventors: Richard Krabetz, Kirchheim; Heinz Engelbach, Limburgerhof, both of Fed. Rep. of Germany

[73] Assignee: BASF Aktiengesellschaft, Ludwigshafen, Fed. Rep. of Germany

[21] Appl. No.: 310,409

[22] Filed: Oct. 9, 1981

Related U.S. Application Data

[63] Continuation of Ser. No. 88,577, Oct. 26, 1979, abandoned, which is a continuation of Ser. No. 859,327, Dec. 12, 1977, abandoned, which is a continuation of Ser. No. 442,492, Feb. 14, 1974, abandoned, which is a continuation-in-part of Ser. No. 11,872, Feb. 16, 1970, Pat. No. 3,845,120.

[30] Foreign Application Priority Data

Feb. 22, 1969 [DE] Fed. Rep. of Germany ....... 1908965

[51] Int. Cl.$^4$ .................... C07C 51/25; C07C 57/055
[52] U.S. Cl. .................... 562/534; 502/312; 562/535; 562/536; 562/600; 568/479
[58] Field of Search ................. 562/535, 534; 502/312

[56] References Cited

U.S. PATENT DOCUMENTS

| | | | |
|---|---|---|---|
| 3,527,797 | 9/1970 | Krabetz et al. | 562/535 |
| 3,644,509 | 2/1972 | Allen | 562/535 |
| 3,711,540 | 11/1973 | Nonnenmacher et al. | 562/534 |
| 3,845,120 | 10/1974 | Krabetz et al. | 562/535 |

*Primary Examiner*—Vivian Garner
*Attorney, Agent, or Firm*—Keil & Weinkauf

[57] ABSTRACT

Production of acrylic acid by oxidation of acrolein with gas containing oxygen in the gas phase at elevated temperature in the presence of a catalyst which, in addition to oxygen, consists essentially of (a) molybdenum, (b) tungsten, (c) vanadium and (d) iron and/or copper. The atomic ratio of molybdenum:tungsten:iron and/or copper is 1 to 20:0.01 to 10:1 and the atomic ratio of vanadium:molybdenum is 0.2 to 6:6. Acrylic acid is an important starting material for the production of high polymers.

7 Claims, No Drawings

PRODUCTION OF ACRYLIC ACID BY OXIDATION OF ACROLEIN

This is a continuation of application Ser. No. 88,577, filed Oct. 26, 1979, now abandoned, which in turn is a continuation of application Ser. No. 859,327, filed Dec. 12, 1977, now abandoned, which in turn is a continuation of application Ser. No. 442,492, filed Feb. 14, 1974, now abandoned, which in turn is a continuation-in-part of application Ser. No. 11,872, filed Feb. 16, 1970, now U.S. Pat. No. 3,845,120.

It is known from Belgian Pat. No. 658,192 that acrylic acid may be obtained by oxidation of acrolein with gas containing oxygen in the presence of catalysts containing molybdenum, tellurium, phosphorus and oxygen. The process has the disadvantage, however, that at the temperature used, tellurium migrates from the catalyst in a short time. The catalyst thus rapidly becomes inactive so that the yield of acrylic acid declines. According to another method which is described in Belgian Pat. No. 610,392 acrolein can be oxidized into acrylic acid in the presence of catalysts containing phosphorus, tungsten, molybdenum and vanadium. It is only at temperatures above 400° C., however, that the process proceeds with good yields. Oxidation of acrolein to acrylic acid in the presence of catalysts is described in other patents. Molybdenum trioxide and basic metals such as cobalt or nickel with additions of boron trioxide or phosphorus pentoxide are used as catalysts according to a process described in U.S. Pat. No. 3,087,964. Metals of group VIb of the Periodic System with additions such as bismuth, tin, cobalt, vanadium, antimony, nickel, titanium or tungsten, are described as suitable catalysts in British Pat. No. 999,836. Furthermore, it is known from U.S. Pat. No. 3,358,020 that catalysts containing iron, molybdenum, vanadium and antimony are suitable. Moreover it is known from British Pat. No. 903,034 that the oxidation of acrolein to acrylic acid will take place in the presence of catalysts which contain molybdenum and one or more than one polyvalent metal such as iron, tungsten, tin or antimony. All catalysts hitherto used for the conversion of acrolein into acrylic acid, however, have the disadvantage that high space-time yields are not achieved.

It is an object of the invention to provide a process for the production of acrylic acid by the oxidation of acrolein with gas containing oxygen in which a higher space-time yield is obtained than in prior methods. Another object of the invention is to provide a process in which yields of acrylic acid of more than 90% are achieved at practically quantitative conversions of acrolein. A further object of the invention is to provide a process in which the catalysts remain active for long periods and which can be carried out at fairly low temperatures.

In accordance with this invention these and other objects and advantages are obtained in a process for the production of acrylic acid by the oxidation of acrolein with gas containing oxygen in the gas phase at elevated temperature in the presence of a catalyst which, in addition to oxygen, consists essentially of (a) molybdenum, (b) tungsten, (c) vanadium and (d) iron and/or copper. In this catalyst, the atomic ratio of molybdenum:tungsten:iron and/or copper is 1 to 20:0.01 to 10:1 and the atomic ratio of vanadium:molybdenum is 0.2 to 6:6.

Pure acrolein may be used for the reaction but it is preferred to use a gas containing acrolein such as is obtained in the production of acrolein by the oxidation of propylene. The gas advantageously has a content of acrolein of from 1 to 20% by volume. Particularly good results are achieved when the gas contains from 2 to 10% by volume of acrolein. In addition to acrolein, the gas may contain for example acrylic acid, acetic acid, formamide, acetaldehyde and small amounts, for example up to 3% by volume, of hydrocarbons such as propylene, propane, butylene or butane. Other gases such as nitrogen, carbon dioxide, steam (for example up to 70% by volume) and oxygen (for example up to 20% by volume) may also be present.

The gas containing oxygen used in the process of the invention generally has an oxygen content of 10 to 30% by volume, advantageously 15 to 25% by volume. It is particularly advantageous to use air. The gas may contain inert constituents such as nitrogen, carbon dioxide or argon, in addition to oxygen.

It is advantageous to use 0.5 to 10, particularly 0.5 to 3, parts by volume of oxygen to 1 part of gaseous acrolein. When using gases containing acrolein (prepared for example by the oxidation of propylene) as starting material, any oxygen present in these gases should be taken into account.

The reaction is advantageously carried out at temperatures of from 220° to 450° C. Particularly good results are obtained by using temperatures of from 240° to 340° C. Bath temperatures of from 200° to 400° C., preferably from 220° to 280° C., are generally used for the reactions. Oxidation is carried out in the gas phase and the residence time of the starting materials at the catalyst should be from 0.1 to 20 seconds, preferably from 1 to 10 seconds.

The atomic ratio of (a) molybdenum:(b) tungsten:(d) iron and/or copper is 1 to 20:0.01 to 10:1 and the atomic ratio of (c) vanadium:(a) molybdenum is 0.2 to 6:6. Preferred catalysts contain (a) molybdenum:(b) tungsten:(d) iron and/or copper in an atomic ratio of 2 to 10:0.1 to 2:1. The preferred catalysts also contain vanadium in an atomic ratio (c) vanadium:(a) molybdenum of 0.5 to 4:6. Particularly good results are obtained by using a catalyst of vanadium, molybdenum, tungsten and iron and/or copper in which the atomic ratio of molybdenum:tungsten:iron and/or copper is 1 to 20:0.01 to 10:1, preferably 2 to 10:0.1 to 2:1 and the atomic ratio of vanadium to molybdenum is 0.2 to 6:6, preferably 0.5 to 4:6. The said metals may be present in the catalyst as a mixture of oxides or as compounds of these oxides with each other.

The catalysts may be prepared for example by allowing aqueous solution of salts of iron and/or copper which are readily converted into the oxides upon heating, for example chlorides or sulfates, to flow into an aqueous solution of ammonium molybdate, ammonium tungstate and ammonium vanadate. The precipitation is advantageously carried out in the presence of nitrogen bases such as ammonia, trimethylamine, pyridine or salts thereof at elevated temperature, for example 50° to 100° C. It has proved to be specially advantageous to maintain a pH of from 4 to 0.5, particularly from 3 to 1.0 during the precipitation. A precipitate separates and this is washed with water and dried for example for ten to fifteen hours at 110° to 130° C. and then heated advantageously for three to twenty hours in a stream of air at 200° to 700° C., preferably from 350° to 450° C. According to another advantageous method, the catalyst may be prepared by mixing oxides of the metals or readily decomposable salts of the metals such as acetates, formates, oxalates, nitrates or ammonium salts of oxyacids of the metals, if necessary converting the salts into the oxides, and then heating the resulting mixture, if desired in a stream of air, advantageously in a stream of nitrogen, at temperatures of for example from 300° to 800° C. In a preferred method of preparing the catalysts, tungstic acid, molybdic acid and vanadium pentoxide or ammonium vanadate are introduced at elevated temperature, for example at 20° to 80° C., into aqueous ammonia solution. The solution obtained is evaporated and the residue if necessary dried at elevated temperature, advantageously at temperatures of from 90° to 140° C., and comminuted. The residue is kneaded with the addition of water and then further kneaded with the nitrates of iron and/or copper, with or without the addition of water in portions. The kneaded material is then dried and thereafter calcined at a rising temperature of from 150° to 450° C., preferably from 200° to 400° C. The calcination may be carried out in the presence of air, although it is preferably carried out in the presence of an inert gas such as steam, argon and particularly nitrogen. In a variant of the preferred embodiment, the evaporated residue of the solution of molybdenum, tungsten and vanadium salts is suspended in water, an aqueous solution of metal nitrates is added and the mixture is advantageously evaporated to dryness, kneaded for example for three to five hours and then dried. The dried residue is then calcined at the temperatures specified above. The catalysts may be applied to carriers such as silicic acid, aluminum oxide or silicates. The supported catalysts advantageously contain 90 to 10%, preferably 70 to 50%, by weight of active catalyst material with reference to the sum of catalyst and carrier.

The process according to this invention may be carried out for example by arranging a catalyst of the said composition as a fixed bed in a reaction tube and passing a mixture of acrolein and gas containing oxygen in the said ratio over the catalyst at the said temperature and with the said residence times. The hot reaction gas obtained may be cooled rapidly and washed, for example with water, the acrylic acid dissolving in the water. Unoxidized acrolein may be deposited, separated from the acrylic acid and returned to the reaction. It is advantageous to recycle the wash water so that acrylic acid accumulates therein. Acrylic acid is then advantageously extracted with an organic solvent such as ethyl acetate from the enriched aqueous solution. After the aqueous phase has been separated, for example by decantation, the acrylic acid is isolated from the extract by distillation.

The following Examples illustrate the invention.

EXAMPLE 1

250 parts of tungstic acid and 920 parts of molybdic acid (94% by weight of molybdenum trioxide) are added in portions in the sequence given to 2,000 parts by volume of a 15% by weight aqueous ammonia solution at 25° to 70° C. 117 parts of ammonium vanadate is added to the solution which may still contain undissolved constituents. The solution obtained is evaporated and dried for about twelve hours at 110° C. The dried material is kneaded for one hour with an addition of water and after 606 parts of iron(III) nitrate (9 moles of water of crystallization) has been added the whole is kneaded for another three hours while adding water in portions. The material thus obtained is dried for twelve hours, calcined for two hours at 100° C., two hours at 300° C. and four hours at 360° C. in a stream of nitrogen, and then broken down. 2% by weight of graphite with reference to the catalyst material is added and the mixture is pressed into pellets having the dimensions 3 mm × 3 mm.

50 parts by volume of the catalyst prepared in this way is arranged as a fixed bed in a reaction tube heated by a melt of mixed alkali metal nitrates. A mixture of 3.1 mole% of acrolein, 0.4 mole% of propylene, 0.48 mole% of acrylic acid and acetic acid, 5.5 mole% of oxygen and 45 mole% of nitrogen together with 43 mole% of steam and minor amounts of oxidation products of propylene such as are formed in the production of acrolein is passed over the catalyst. The saltpeter bath is kept at a temperature of 250° C. According to gas chromatographic analysis, a conversion of 99 mole% is achieved with reference to acrolein used. The yield of acrylic acid is 91 mole%.

The above procedure is followed but 25 parts by volume of the catalyst is used and the temperature is kept at 245° C. Gas chromatographic analysis indicates a conversion of 98.5 mole% of acrolein, a yield of 90% of acrylic acid being achieved.

COMPARATIVE EXAMPLE (a)

The procedure described in Example 1 is followed but no ammonium vanadate is added. At 230° C. a conversion of 94 mole% and a yield of 85 mole% are achieved with 50 parts by volume of the catalyst thus prepared. At 245° C. a conversion of 89 mole% of acrolein and a yield of 83% of acrylic acid are obtained with 25 parts by volume of the catalyst.

COMPARATIVE EXAMPLE (b)

42.4 parts of ammonium molybdate, 7.0 parts of ammonium vanadate and 6.1 parts of ammonium tungstate are dissolved separately in water and the aqueous solutions are combined. The suspension thus obtained is dried and powdered. Tablets are pressed from the powder and these are calcined for five hours at 400° C.

50 parts by volume of the catalyst prepared in this way is arranged as a fixed bed in a reaction tube which is heated by a melt of mixed alkali metal nitrates. A mixture of 3.1 mole% of acrolein, 0.4 mole% of propylene, 0.48 mole% of acrylic acid and acetic acid, 5.5 mole% of oxygen, 45 mole% of nitrogen and 43 mole% of steam as well as minor amounts of oxidation products of propylene such as occur in the production of acrolein, is passed over the catalyst. A temperature of 230° C. is maintained in the saltpeter bath. According to gas chromatographic analysis a conversion of 55 mole% with reference to acrolein used is achieved and a yield of acrylic acid of 43 mole%.

If the reaction temperature is raised to 250° C., a conversion of 90% with reference to the acrolein used and a yield of acrylic acid of 69 mole% are achieved.

EXAMPLES 2 TO 8

Molybdenum/tungsten/vanadium/iron catalysts which have been prepared according to Example 1 and in which the atomic ratio is varied are installed in an amount of 50 parts by volume in a reactor (2) located downstream of a reactor (1). Reactor (1) contains 50 parts by volume of an oxidation catalyst for the oxidation of propylene to acrolein. A mixture of 3,300 parts by volume of propylene, 40,000 parts by volume of air and 18,700 parts by volume of steam is passed into the first reactor. The temperature of the first reactor is controlled so that propylene is converted to a gas mixture containing acrolein which has the composition given in Example 1. The gas mixture is passed through reactor (2) and the bath temperature is adjusted to that specified in the Examples in each case. The conversion and yields, with reference to the propylene passed into reactor (1), are given in the Table.

The following abbreviations are used in Table I:
Ex=Example No.
Mo:W:V:Fe=atomic ratio Mo:W:V:Fe in each catalyst used
Temp=bath temperature of reactor (2) in °C.
Conv=conversion of propylene in mole%
AcrA=acrylic acid
Ace=acetic acid
Mal=maleic acid
RAc=residual acrolein

TABLE I

| Ex | Mo:W:V:Fe | Temp | Yields in mole %: | | | | |
|---|---|---|---|---|---|---|---|
| | | | Conv | AcrA | Ace | Mal | RAc | CO/CO$_2$ |
| 2 | 6:1:1:1.75 | 240 | 95.2 | 62.9 | 4.3 | 5.7 | 0.1 | 17.3 |
| 3 | 6:1:1:1.5 | 240 | 95 | 65 | 3.9 | — | 1.0 | 18.5 |
| 4 | 6:1:1:1.25 | 241 | 95.1 | 62.6 | 6.2 | 7.3 | 1.8 | 17.2 |
| 5 | 6:1:1:1 | 240 | 95 | 55 | — | — | 8.0 | — |
| 6 | 6:1:1:1.5 | 230 to 240 | 97.2 | 64.9 | 6.1 | — | 1.2 | 20 |
| 7 | 6:1:2:1.5 | 230 to 240 | 97.2 | 65.0 | 7.2 | — | 1.8 | 22.1 |
| 8 | 6:1:3:1.5 | 230 to 240 | 97.2 | 60.6 | 4.0 | — | 2.6 | 26.2 |

EXAMPLES 9 AND 10

The procedure described in Examples 2 to 8 is followed and the catalysts specified in the following Table are used with the compositions specified and with the stated bath temperatures. The conversions and yields indicated are achieved.

The following abbreviations are used in Tables II, III and IV:
Ex=Example No.
Composition=composition of catalyst apart from oxygen
BT=bath temperature in °C.
Co=conversion in mole%
AcrA=acrylic acid
Sel=selectivity
Ace=acetic acid
RAc=residual acrolein

TABLE II

| Ex | Composition | Atomic ratio | BT | Co | Yield in mole % | | |
|---|---|---|---|---|---|---|---|
| | | | | | AcrA | Ace | Sel |
| 9 | Mo:W:V:Cu:Mn | 6:1:1.5:0.75:0.75 | 270 | 93 | 55 | 12.5 | 0.5 |
| 10 | Mo:W:V:Cu:Ni | 6:1:1.5:0.75:0.75 | 270 | 93 | 63.3 | 5.5 | 2 |

EXAMPLES 11 TO 14

In each case, 61 parts by weight of ammonium paratungstate, 70 parts by weight of ammonium meta-vanadate and 424 parts by weight of ammonium heptamolybdate are introduced into 3000 parts by weight of boiling water. Then solutions of varying amounts (e.g. 119 parts in Example 11) of copper(II) nitrate in 300 parts of water are poured in rapidly while stirring, 1032 parts by weight of finely powdered α-alumina is introduced into each of the mixtures. The suspensions thus obtained are evaporated to dryness on a waterbath. The compositions are then kneaded for 3½ hours, each with 560 parts of water, dried and calcined first at rising temperatures between 200° C. and 250° C. in air for 6 hours and then at 400° C. in air for 3 hours.

The ratios of catalyst components are indicated in Table III below.

In each case, 40 cm$^3$ of the catalyst in the form of particles 2 to 4 mm in diameter is placed in a steel tube having a diameter of 15 mm and heated to from 290° to 330° C. 4.8 l of acrolein, 28 l of air, 30 l of nitrogen and 25 l of steam are passed per hour through the tube. The resulting acrolein conversions as well as yields and selectivities in respect of acrylic acid are given in Table III below.

TABLE III

| | Composition | | | AcrA | |
|---|---|---|---|---|---|
| Ex | Cu:Mo:W:V | BT | CO | Yield mole % | Sel mol % |
| 11 | 1.2:6:0.6:1.5 | 290 | 97 | 91 | 93.8 |
| 12 | 1.5:6:0.6:1.5 | 310 | 97 | 88 | 90.7 |
| | | 316 | 98 | 90 | 91.8 |
| 13 | 0.75:6:0.6:1.5 | 330 | 94 | 75 | 79.8 |
| 14 | 3:6:0.6:1.5 | 295 | 96 | 81.6 | 85 |

EXAMPLE 15

A catalyst is prepared as described in Example 1, except that a mixture of iron(III) nitrate and copper(II) nitrate is used instead of iron(III) nitrate, in such an amount that in the finished catalyst the atomic ratio Fe:Cu:Mo:W:V = 0.75:0.75:6:1:1.5.

A mixture of 5.4 l of acrolein, 32 l of air, 70 l of nitrogen and 30 l of steam is passed over 50 cm$^3$ of the catalyst at 280° C. (the figures in liters referring to 20° C. and atmospheric pressure). At an acrolein conversion of 98 mole%, 85% of the acrolein employed or 87% of the acrolein reacted is oxidized to acrylic acid.

EXAMPLES 16 AND 17 AND COMPARATIVE EXAMPLES c, d AND e

To compare the catalysts of the invention with the catalysts according to U.S. Pat. Nos. 3,595,911 and 3,644,509 and German Laid-Open Specification 1,518,697, 40 cm$^3$ of each of the catalysts indicated in Table IV below in the form of particles 2 to 4 mm in diameter was heated to 350° C. in an iron tube having an internal diameter of 15 mm. At this temperature a mixture of 5.4 l of acrolein, 48 l of air and 40 l of steam (measured at 20° C. and atmospheric pressure) was passed per hour through the tube. The quantities of acrolein and acrylic acid contained in the reaction mixture leaving the tube were determined and the conversion of acrolein, the yield of acrylic acid and the selectivity of the catalysts were calculated from them according to the following equations:

$$\text{Conversion} = \frac{\text{moles of acrolein reacted} \times 100}{\text{moles of acrolein introduced}}$$

$$\text{Yield of acrylic acid} = \frac{\text{moles of acrylic acid formed} \times 100}{\text{moles of acrolein introduced}}$$

$$\text{Selectivity} = \frac{\text{moles of acrylic acid formed} \times 100}{\text{moles of acrolein reacted}}$$

The results obtained are shown in the following Table IV:

TABLE IV

| Ex. | Catalyst | Composition | BT | Conversion of acrolein mole % | Yield of AcrA | Sel AcrA |
|---|---|---|---|---|---|---|
| c | Example 3 of U.S. Pat. No. 3,595,911 (Ball) | Sb:Cu:Mo = 4:1:0.5 | 270 | <5 | <5 | <5 |
|  |  |  | 340 | 20 | 7.3 | 36.5 |
|  |  |  | 350 | 34 | 9.1 | 27 |
|  |  |  | 360 | 34 | 3.4 | 10 |
| d | Example 11 of German Laid-Open Specification 1,518,697 (v.d. Meer) | Sb:Cu:Sn:V = 2:0.25:1:1 | 270 | <5 | <5 | <5 |
|  |  |  | 340 | 25 | 16.5 | 66 |
|  |  |  | 360 | 36 | 11 | 31 |
| e | Example D of U.S. Pat. No. 3,644,509 (Allen) | Mn:Mo:W:V = 1.5:6:0.6:1.5 | 270 | 89 | 75 | 84 |
|  |  |  | 280 | 94 | 74 | 79 |
|  |  |  | 290 | 99 | 74 | 75 |
| 16 | Present invention (of. footnote (1)) | Cu:Mo:W:V = 1.5:6:0.6:1.5 | 280 | 45 | 50 | 90 |
|  |  |  | 310 | 93 | 81 | 87 |
|  |  |  | 320 | 100 | 83 | 83 |
| 17 | Present invention | Fe:Mo:W:V = 1.5:6:0.6:1.5 | 260 | 99 | 85 | 86 |
|  |  |  | 240 | 94 | 81.0 | 86 |

TABLE IV-continued

| Ex. | Catalyst | Composition | BT | Conversion of acrolein mole % | Yield of AcrA | Sel AcrA |
|---|---|---|---|---|---|---|
| Example 1 |  |  |  |  |  |  |

(1) The catalyst for Example 16 was prepared as described in Example D of U.S. Pat. No. 3,644,509 except that copper nitrate (Cu(NO$_3$)$_2$ . 6H$_2$O) was used instead of manganese acetate.

We claim:

1. A process for the production of acrylic acid which comprises oxidizing acrolein with a gas containing oxygen in the gas phase at elevated temperature and in the presence of a catalyst which, in addition to oxygen, consists essentially of (a) molybdenum, (b) tungsten, (c) vanadium and at least one member (d) selected from the group consisting of iron and copper wherein the atomic ratio of (a):(b):(d) is 1 to 20:0.01 to 10:1 and the atomic ratio of vanadium:molybdenum is 0.2 to 6:6.

2. The process of claim 1 wherein said catalyst consists essentially of (a) molybdenum, (b) tungsten, (c) vanadium and (d) iron.

3. The process of claim 2 wherein the atomic ratio of (a):(b):(d) is 2 to 10:0.1 to 2:1 and the atomic ratio of vanadium:molybdenum is 0.5 to 4:6.

4. The process of claim 3, wherein the acrolein is provided to the reaction as a gas containing from about 2 to 10% acrolein by volume and wherein the gas containing oxygen has an oxygen content of from about 15 to 25% oxygen, and which is conducted at a temperature between about 240° and 340° C.

5. The process of claim 1 wherein said catalyst consists essentially of (a) molybdenum, (b) tungsten, (c) vanadium and (d) copper.

6. A process as claimed in claim 5 wherein the atomic ratio of (a):(b):(d) is 2 to 10:0.1 to 2:1 and the atomic ratio of vanadium:molybdenum is 0.5 to 4:6.

7. The process of claim 6, wherein the acrolein is provided to the reaction as a gas containing from about 2 to 10% acrolein by volume and wherein the gas containing oxygen has an oxygen content of from about 15 to 25% oxygen, and which is conducted at a temperature between about 240° and 340° C.

* * * * *